(12) United States Patent
Harlan

(10) Patent No.: US 10,314,670 B2
(45) Date of Patent: Jun. 11, 2019

(54) ADJUSTABLE DENTAL MIRROR

(71) Applicant: Acuity Innovation and Design, LLC, Scottsdale, AZ (US)

(72) Inventor: Laurence Harlan, Scottsdale, AZ (US)

(73) Assignee: Acuity Innovation and Design, LLC, Scottsdale, AZ (US)

( * ) Notice: Subject to any disclaimer, the term of this patent is extended or adjusted under 35 U.S.C. 154(b) by 32 days.

(21) Appl. No.: 15/728,433

(22) Filed: Oct. 9, 2017

(65) Prior Publication Data
US 2018/0153641 A1   Jun. 7, 2018

Related U.S. Application Data

(60) Provisional application No. 62/429,857, filed on Dec. 4, 2016.

(51) Int. Cl.
*A61C 3/00*       (2006.01)
*A61B 1/247*    (2006.01)

(52) U.S. Cl.
CPC ............ *A61C 3/00* (2013.01); *A61B 1/247* (2013.01)

(58) Field of Classification Search
CPC ........... A61B 1/247; A61B 1/24; A61B 1/253; A61C 3/00
See application file for complete search history.

(56) References Cited

U.S. PATENT DOCUMENTS

| 470,211 A | 3/1892 | Philips | |
| 4,212,105 A * | 7/1980 | Hukuba | A61B 1/247 433/30 |
| 4,512,635 A * | 4/1985 | Melde | G02B 7/182 359/882 |
| 5,230,622 A * | 7/1993 | Brossoit | A61B 1/0014 433/30 |
| 5,428,484 A * | 6/1995 | Baker | A61B 1/247 359/872 |
| 5,458,486 A * | 10/1995 | Ballard | A61B 1/247 433/30 |
| 5,636,918 A * | 6/1997 | Lott | A61B 1/24 362/139 |

(Continued)

OTHER PUBLICATIONS

Enbar, Telescoping Mirror for sale on Amazon.com, downloaded Sep. 18, 2017.

(Continued)

*Primary Examiner* — Nicholas D Lucchesi
(74) *Attorney, Agent, or Firm* — Etherton Law Group, LLC

(57) ABSTRACT

A dental mirror permits the mirror face to be flipped from a first angle to a second angle relative to the handle, while the tool is still in the patient's mouth. Mirror and handle connect at a pivot point that is spaced away from the handle's distal end. The neck of the mirror has a detent nub that mates with recesses in the neck of the handle for positioning and holding the mirror in place relative to the handle. The mirror can be shifted from one position to another by pushing or pulling the mirror against the patient's cheek while the mirror is still in the patient's mouth, as the nub slides from one recess to another. In one embodiment the mirror is flipped from a position 145 degrees relative to the handle to 90 degrees relative to the handle. Stops are incorporated to limit angular travel at either position.

10 Claims, 5 Drawing Sheets

(56) References Cited

U.S. PATENT DOCUMENTS

| | | | | |
|---|---|---|---|---|
| 6,050,939 A * | 4/2000 | Pak Wai | ............... | A61B 1/247 |
| | | | | 433/30 |
| 6,666,682 B1 | 12/2003 | Meyerhoff | | |
| 6,698,906 B1 | 3/2004 | Tally | | |
| 8,651,862 B2 | 2/2014 | Solomon | | |
| 8,801,433 B1 | 8/2014 | Charlton | | |
| 2004/0017626 A1 * | 1/2004 | Kasem | .................. | A61B 1/247 |
| | | | | 359/881 |
| 2012/0021373 A1 * | 1/2012 | Moreno | ............... | A61B 1/015 |
| | | | | 433/31 |
| 2012/0244486 A1 * | 9/2012 | Solomon | ................. | A61C 3/00 |
| | | | | 433/3 |
| 2013/0096457 A1 * | 4/2013 | Qiu | ...................... | A61B 1/267 |
| | | | | 600/549 |

OTHER PUBLICATIONS

Osung DMS39 Dental Tilting Mouth Mirror for sale on Amazon.com, downloaded Sep. 18, 2017.
SE801TMC TElescopic Mirror Adjustable, for sale on Amazon.com, downloaded Sep. 18, 2017.

* cited by examiner

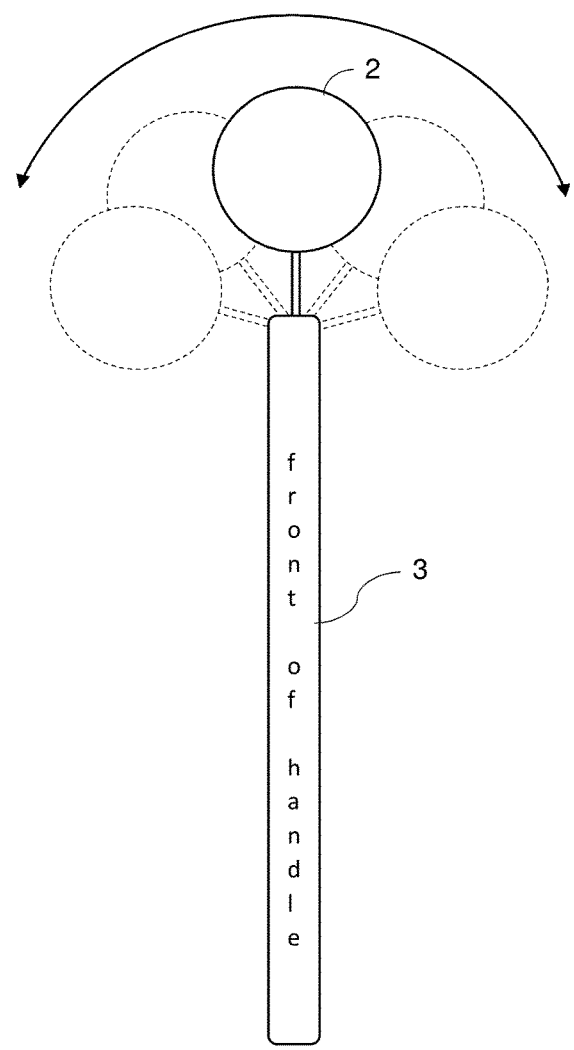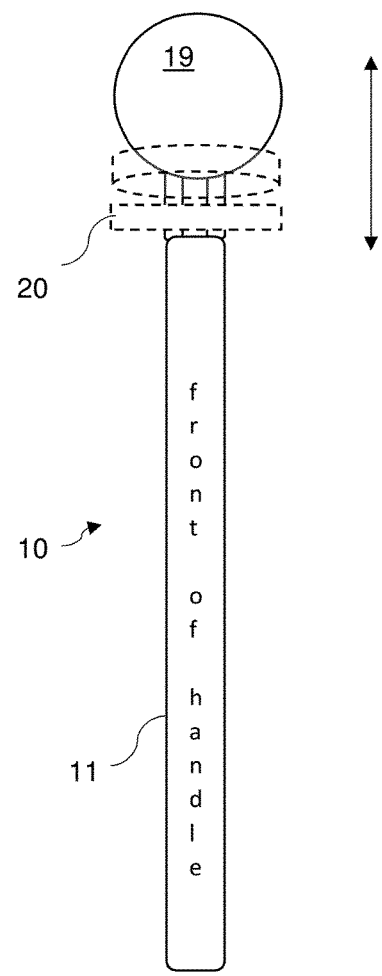
FIG. 1
PRIOR ART
FIG. 2

ADJUSTABLE DENTAL MIRROR

CROSS-REFERENCE TO RELATED APPLICATIONS

This application claims the benefit of U.S. Provisional Application No. 62/429,857 filed Dec. 4, 2016.

FIELD OF INVENTION

This invention relates to dental devices used inside a patient's mouth. This invention relates particularly to an adjustable dental mirror.

BACKGROUND

Dental mirrors are used by dentists, dental hygienists, and other practitioners to allow indirect vision inside the mouth, reflect light onto desired surfaces, and retract soft tissue. Typically the mirror is at a fixed angle relative to the handle, which renders many positions ergonomically challenging and can lead to practitioner fatigue and unnecessarily long procedure times. Some dental mirrors purport to address these problems by enabling the mirror to tilt from side to side, but that mimics manual rotation of the tool in the patient's mouth and similarly leads to awkward positions for the practitioner.

The challenge with existing dental mirrors is that they do not permit the angle of the face of the mirror to be changed relative to the handle, which would be useful to change the angle of reflection and thereby change the surface seen in the mirror. Although existing dental mirrors are available with mirrors fixed at different angles relative to the handle, changing the angle of reflection requires removing the tool from a patient's mouth and inserting a different tool. It would be desirable to have a dental mirror than lets the practitioner change the angle of reflection of the mirror while the tool is in the patient's mouth.

SUMMARY OF THE INVENTION

This invention is a dental mirror that permits the mirror face to be flipped from a first angle to a second angle relative to the handle, while the tool is still in the patient's mouth. In the preferred embodiment, the invention comprises a handle and a mirror. The mirror and handle connect at a pivot point that is spaced away from the distal end of the handle toward the middle of the handle, which minimizes the space the mirror takes up in the mouth. The neck of the mirror has a detent nub that mates with recesses in the neck of the handle for positioning and holding the mirror in place relative to the handle. The mirror can be shifted from one position to another by pushing or pulling the mirror gently against the patient's cheek while the mirror is still in the patient's mouth, as the nub slides from one recess to another. In a preferred embodiment the mirror can be flipped from a position at 145 degrees relative to the handle to 90 degrees relative to the handle. Stops are also incorporated to limit angular travel at either position.

BRIEF DESCRIPTION OF THE DRAWINGS

FIG. 1 is a front view of a prior art dental mirror with a mirror that tilts from side to side.

FIG. 2 is a front view of the present dental mirror with a mirror that pivots from front to back.

DETAILED DESCRIPTION OF THE INVENTION

Figure 3:
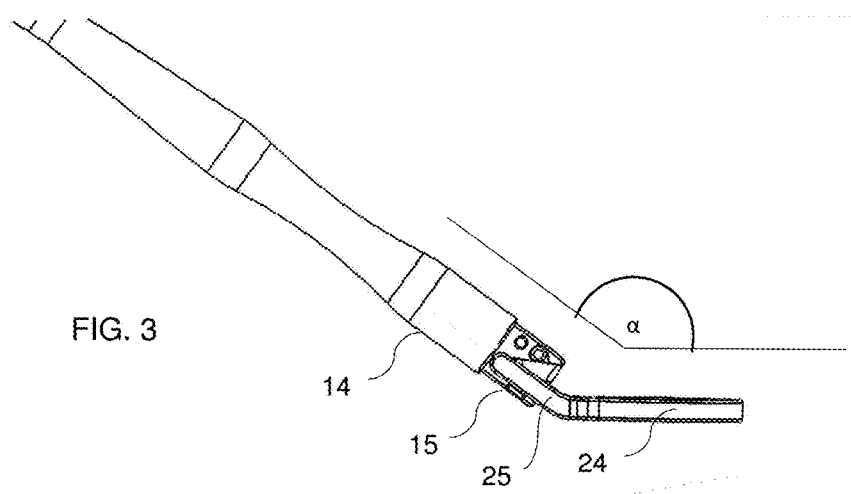
FIG. 3 is a side view of one embodiment of the present dental mirror with the mirror face at angle α relative to the handle.

The present invention is an adjustable dental mirror designated generally as 10. FIG. 1 illustrates a prior art dental mirror in which the mirror 2 tilts side to side relative to the front of the handle 3, with the mirror face staying in the same plane relative to the handle. In contrast, FIG. 2 illustrates the present mirror 10 in which the mirror 20 moves from a first angle to a second angle relative to the front of the handle 11, moving the face 19 of the mirror out of the plane of the handle 11.

Figure 5:
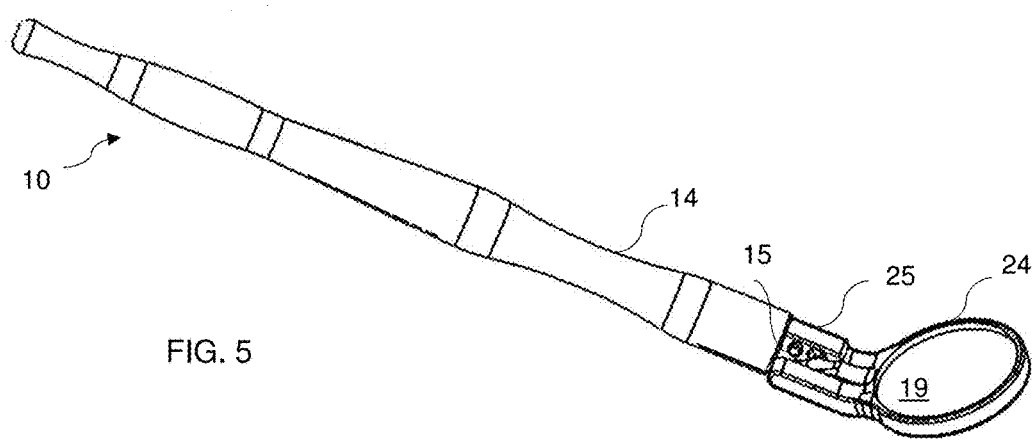
FIG. 5 is a perspective view of the embodiment of FIG. 3 with the mirror at angle α.
Figure 6:
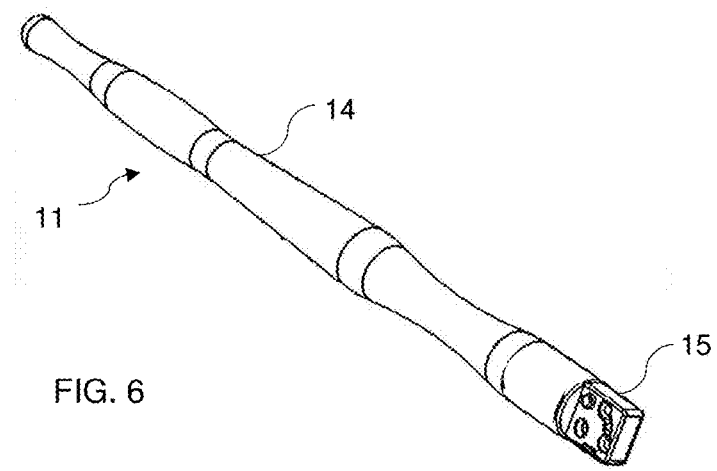
FIG. 6 is a right perspective view of the handle.

In the preferred embodiment, the dental mirror comprises a handle 11, a mirror 20, and a mirror face 19. See FIG. 5. The handle 11 comprises a body 14 and a neck 15 at its distal end. Preferably the handle 11 is shaped to fit comfortably in the practitioner's hand, for example with a constant circular cross-section or with a varying circular or oval cross-sections resulting in a curved outer surface. Preferably the handle 11 is unibody, with the body and neck made of a single piece of material.

Figure 8:
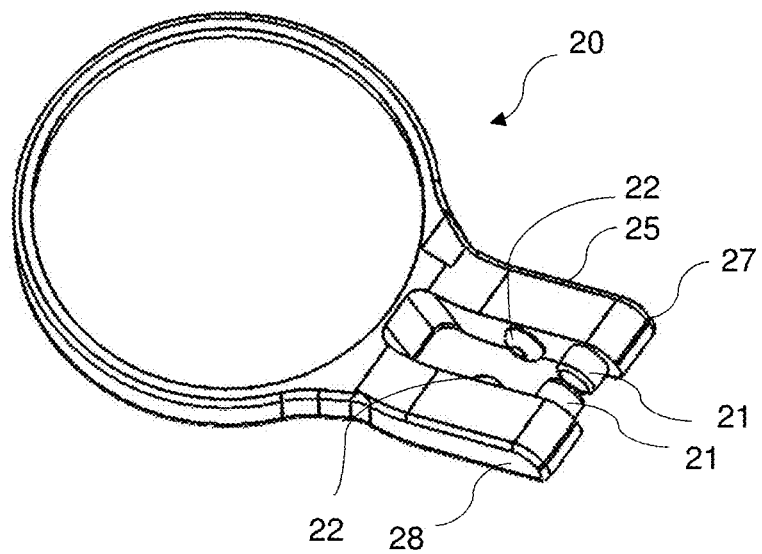
FIG. 8 is a top perspective view of a mirror.
Figure 9:
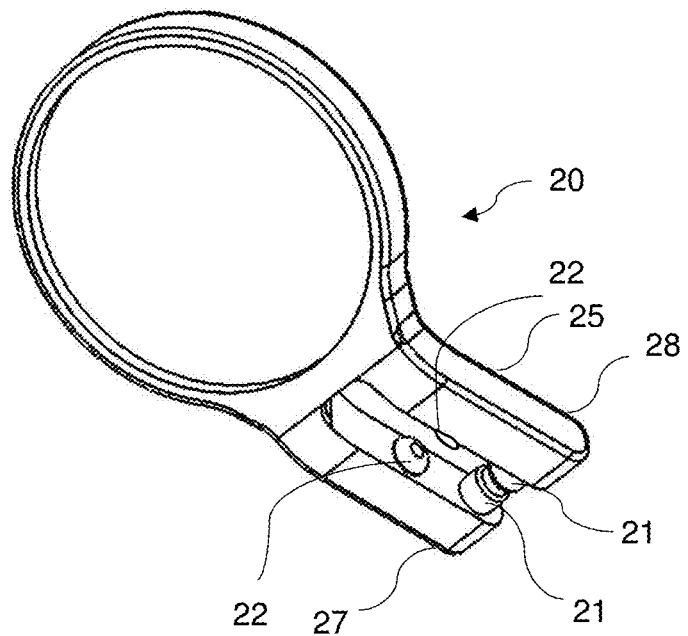
FIG. 9 is a bottom perspective view of the mirror of FIG. 8.
Figure 10:
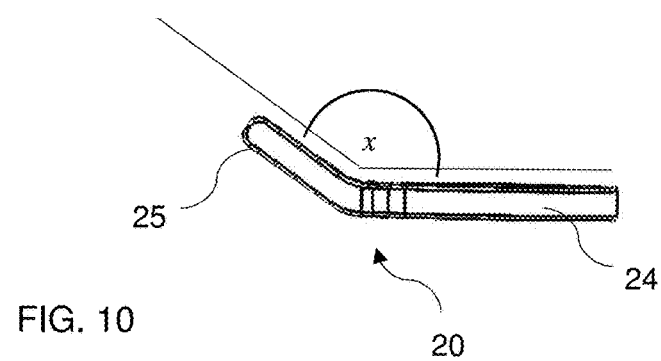
FIG. 10 is a side view of the mirror.
Figure 11:
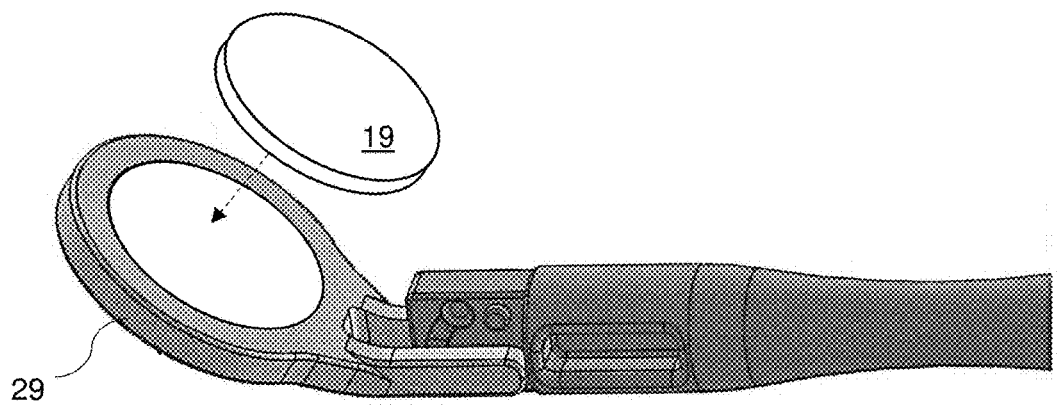
FIG. 11 is a perspective view showing an alternative mirror.

The mirror 20 comprises a head 24 and a mirror neck 25. See FIGS. 8 and 9. The head 24 is typically a housing or hollow frame 29 into which the mirror face 19 is set by snap fit. See FIG. 11. The mirror face 19 may be replaceable. In other embodiments the head 24 is solid and the mirror face 19 is adhered to the surface of the head. Typically the head 24 is round, but may be oval, rectangular or other shape. The mirror neck 25 intersects the head 24 at an obtuse angle x, as illustrated in FIG. 10. Preferably the angle x is 145 degrees.

The neck 15 of the handle and the mirror neck 25 cooperate to form a hinge that permits the angle between the head 24 and the handle 11 to open and close. See FIGS. 3 and 4. The neck 15 of the handle 11 and the mirror neck 25 can be configured in many ways to form a hinge, such as a ball joint or a U-joint. In the preferred embodiment the handle neck 15 is configured to connect to the mirror neck 25 at a pivot point to form the hinge. The pivot point is spaced away from the distal end of the handle toward the middle of the handle, which minimizes the space the mirror takes up in the mouth in its angled positions.

Figure 7A:
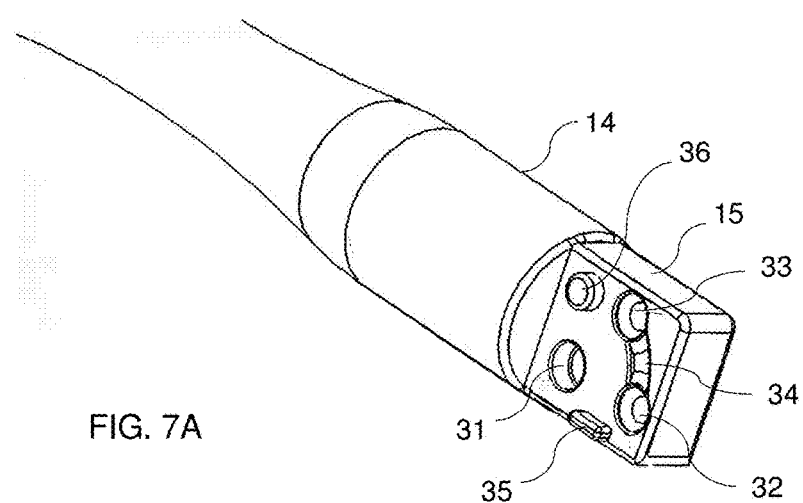
FIG. 7A is a close-up perspective view of the right side of the handle of FIG. 6.
Figure 7B:
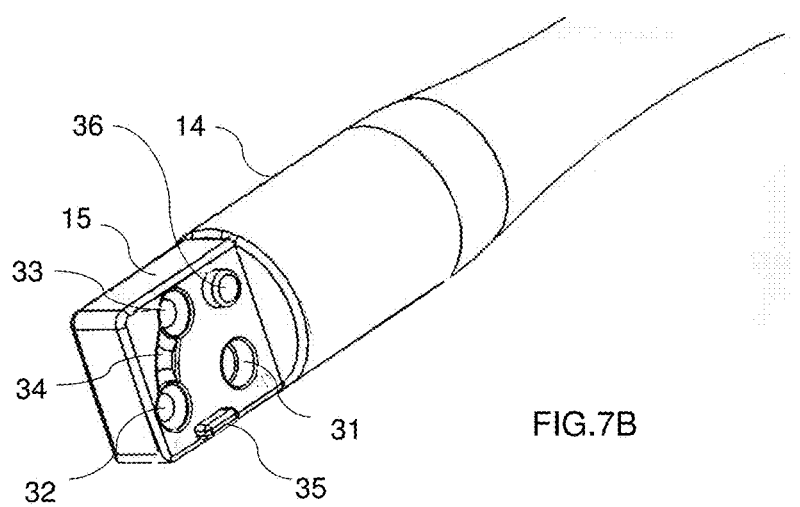
FIG. 7B is a close-up perspective view of the left side of the handle of FIG. 6.

The neck 15 has a pivot recess 31 to receive a pivot nub 21 from the mirror neck 25. See FIGS. 7A-B. In the preferred embodiment the pivot recess 31 is a through-hole through the neck 15, but in some embodiments the pivot recess 31 may be a recess in one side of the neck 25 or both sides. In other embodiments the disposition of the recesses and nubs may be reversed, where the pivot nub is on the mirror neck 25 and the pivot recess is in the neck 15.

The neck 15 of the handle and the mirror neck 25 also cooperate to position and retain the mirror 20 in place relative to the handle 11. The neck 15 has a detent recess 32 to receive a detent protuberance or boss 22 which together use friction to hold the mirror neck 25 in a position defined by the location of the recesses 32 and bosses 22. The neck 15 has a second detent recess 33 to receive the boss 22, which cooperate to hold the mirror in a second position relative to the handle. In one embodiment the recesses are connected by a slide channel 34 that helps guide the boss 22 from one recess to the next. The recesses 32 and 33 may be in one side of the neck 25, but are preferably on both sides for added stability and sturdiness. In other embodiments the disposition of the recesses and bosses may be reversed, where the recesses are on the mirror neck 25 and the bosses are on the neck 15.

In a preferred embodiment the mirror neck has two legs 27 and 28 from which the bosses and pivot nubs extend. See FIGS. 8 and 9. The neck 15 of the handle fits between the two legs and snaps into place, permitting the mirror to pivot about the pivot point from one detent to the next.

In lieu of a boss and recess, the detent may be formed by another mechanical arrangement such as a catch, dog, or spring-operated ball for positioning and holding the mirror at an angle to the handle such that the device can be released by force applied to one of the parts. Preferably the parts may move in both directions against one another instead of in only one direction. Alternative methods to retain the mirror in a desired position can be employed, such as having a positive lock with a button release located within the handle.

Figure 4:
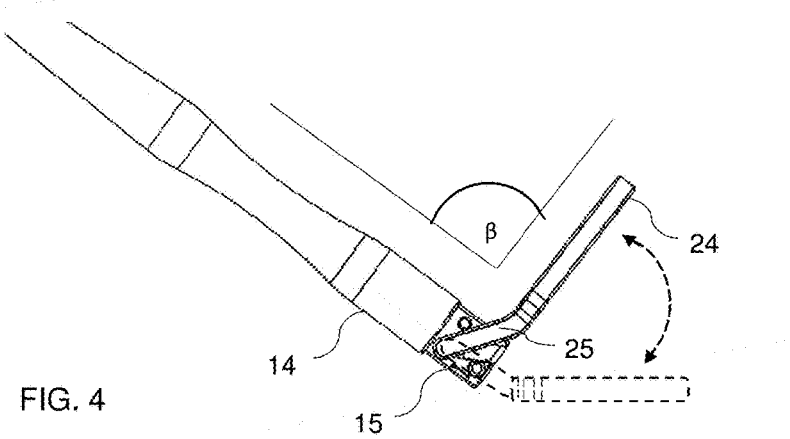
FIG. 4 is a side view of the embodiment of FIG. 3 with the mirror at angle β.

FIG. 3 shows the angle α between the head 24 and the longitudinal axis of the handle 11 at about 145 degrees. FIG. 4 shows the head moved to a new position in which the angle β between the head 24 and the longitudinal axis of the handle 11 is about 90 degrees. The angular positions can also be more or less than 145 and 90 degrees, and additional recesses 23 and mated bosses may be located in any number of locations to achieve different angular positions. In one embodiment the pivot point is in the center of the neck with detents surrounding the pivot point. A first stop 35 on one side of the pivot point and a second stop 36 on the other side of the pivot point are also incorporated to limit angular travel at either position as determined by the location of the stops.

The device 10 is made from biocompatible materials which are pharmacologically inert, nontoxic, and sterilizable. The materials can be plastic or metallic, such as stainless steel or titanium. Preferably the mirror face is glass and the handle and mirror head are made of a polycarbonate plastic.

The above described invention allows the practitioner to adjust the angle of the reflected image for better visualization. In use, the mirror is moved from the first position to the second position by pressing it with sufficient force to overcome the friction of the detents, and preferably that force is small enough to be obtained by the practitioner pressing the mirror on the patient's cheek or other mouth tissue so that the practitioner does not have to remove the tool from the mouth. The mirror can be moved back to the first position, by again pressing it with sufficient force to overcome the friction of the detents. Additionally, the ability to change the angle of the mirror relative to the handle facilitates improved retraction of both the tongue and cheek. This is particularly useful for dentists and dental hygienists when working on a patient's lower arch.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

I claim:

1. An adjustable dental mirror comprising:
    a) a mirror having a face, a mirror neck and a head; and
    b) a handle having a handle body and a handle neck;
    wherein the mirror is connected at the mirror neck to the handle neck at a pivot point such that the angle between the mirror face and the handle changes when the mirror pivots relative to the handle; and
    wherein:
    the handle neck has two or more recesses to receive two or more mated protuberances on the mirror neck such that the mirror is retained in position at each recess.

2. The dental mirror of claim 1 wherein a first recess of the recesses retains the mirror at 145 degrees relative to the handle and a second recess of the recesses retains the mirror at 90 degrees relative to the handle.

3. The dental mirror of claim 1 wherein the handle is unibody.

4. An adjustable dental mirror comprising:
    a) a handle comprising:
        i. a handle body;
        ii. a handle neck extending along the longitudinal axis of the handle body, the handle neck comprising a first surface with two or more first recesses and a first channel connecting the recesses; and
    b) a mirror pivotably connected to the handle, the mirror comprising:
        i. a head and a mirror neck, where the mirror neck further comprises a first protuberance that slides in the first channel and mates with the two or more first recesses; and
        ii. a mirror face connected to the mirror.

5. The dental mirror of claim 4 wherein a first recess of the first recesses retains the mirror at 145 degrees relative to the handle and a second recess of the first recesses retains the mirror at 90 degrees relative to the handle.

6. The dental mirror of claim 4 wherein:
    a) the handle neck further comprises a pivot hole; and
    b) the mirror neck further comprises a first pivot nub;
    wherein the first pivot nub mates with the pivot hole to pivotably connect the handle neck with the mirror neck.

7. The adjustable dental mirror of claim 6 wherein:
    a) the handle neck comprises a second surface opposite the first surface, the second surface having two or more second recesses and a second channel between the second recesses; and
    b) the mirror neck further comprises a second protuberance that slides in the second channel and mates with the two or more second recesses and a second pivot nub that mates with the pivot hole to pivotably connect the handle neck with the mirror neck.

8. The dental mirror of claim 7 wherein:
    a) the mirror neck comprises a first leg from which the first protuberance and pivot nub extend and a second leg from which the second protuberances extends; and
    b) the handle neck fits between the first leg and the second leg.

9. The dental mirror of claim 4 wherein the handle is unibody.

10. The dental mirror of claim 4 wherein the mirror is unibody.

\* \* \* \* \*